March 30, 1976 J. W. HINES Plant Pat. 3,855
AZALEA PLANT
Filed Nov. 25, 1974
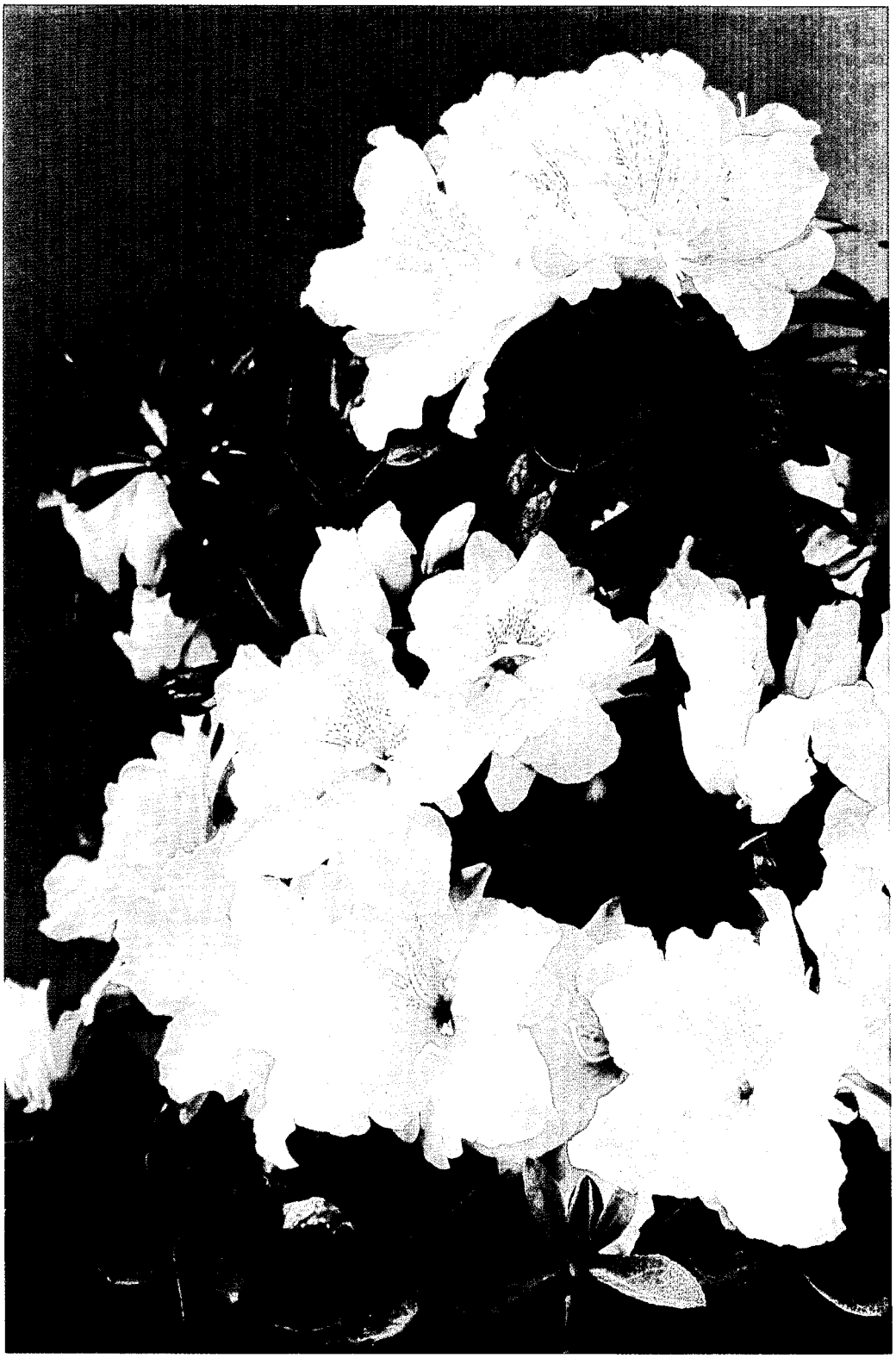

United States Patent

Plant Pat. 3,855

Patented Mar. 30, 1976

3,855

AZALEA PLANT

James W. Hines, Jr., Corona Del Mar. Calif. assignor to Hines Wholesale Nurseries, Santa Ana, Calif.

Filed Nov. 25, 1974, Ser. No. 526,639

Int. Cl. A01h *5/00*

U.S. Cl. Plt.—55 1 Claim

The present invention relates to a new and distinct variety of azalea plant. I discovered this new variety on my cultivated property at 12621 Jeffrey Road, in the city of Santa Ana, county of Orange, State of California, in December 1970. This new variety originated as a sport of Azalea "Rose Queen," an unpatented variety of the Rutherfordiana strain.

My discovery of this sport was occasioned by the fact that at the time aforementioned, I was growing a great many azaleas of the variety A. "Rose Queen" under my direction and control in the nursery of my assignee, located in Santa Ana, Calif., in which I held and still hold a partnership interest. While observing and supervising the growth and cultivation of these plants, I observed that one plant bore, in part, the rose-pink flowers of A. "Rose Queen," while several branches had sported and displayed flowers which were predominantly, and almost entirely, white. I isolated this plant, and made numerous cuttings from the branches that bore the white flowers. I kept the mother plant and the cuttings made therefrom under close observation. The outstanding color characteristics of the branches that had sported, and the cuttings grown therefrom, were confirmed by these tests, that in subsequent blooming the color variation referred to remained true for succeeding generations. However, observation has confirmed that, other than color variation, which come true by asexual reproduction, the new variety while retaining characteristics which conform to its parent, it possesses qualities which distinguish it otherwise from its parent, and other varieties of which I am aware.

My new azalea variety is characterized as to novelty by the clean-looking white coloration of its flowers profusely growing and outstanding with its background of rich green foliage; by its almost simultaneous full-bloom appearance toward the end of December even without forcing; by its compact and thickly branched habit of growth; and by its Rutherfordiana parentage which inherently produces large flowers.

In the accompanying drawing a section of the plant showing typical blooms and foliage appears in reduced scale. These are portrayed in color as fairly as can be obtained by this method of illustration.

In the following detailed description of the new variety, to facilitate identification, I have used the color terminology of the R. H. S. Colour Chart issued by the Royal Horticultural Society of London.

Locality where grown and observed: On the Irvine Ranch, approximately 5 miles south of Santa Ana, Calif.

Parentage: Sport of Azalea "Rose Queen," an unpatented variety.

Propagation: No variation from its distinguishing characteristics through succeeding generations propagated by cuttings. Cannot be propagated from seed.

THE PLANT

Growth: The plant is of very vigorous growth habit, with dense branching starting just above ground level. Flowering is prolific, with first blooms appearing in the early part of December, and a heavy burst of bloom by the last week of December. Bloom is continuous thereafter to mid-March.

Branches: New growth is in the Yellow-Green Group, Plates 152B to 152C, gradually changing in color toward the tip to Yellow-Green Group, Plates 144B to 144C. Older branches are in the Greyed-Orange Group, Plates 166A to 166B. All branches are hirsute.

Foliage: The leaves are of good substance, semi-glossy and abundant.

Shape: Elliptic with an obtuse tip, and a slightly undulating surface. Leaf margins are entire and slightly hairy.

Color:

*New leaves.*—Upper surface is in the Yellow-Green Group, Plates 144A to 144B. Underside is in the Yellow-Green, also Plates 144B to 144C.

*Mature leaves.*—Upper surface is in the Green Group, Plates 137A to 137B. Underside is in the Yellow-Green Group, Plates 146B to 146C.

Size: New leaves are from 1 to 1¼ inches in width, and 2 to 2¼ inches in length. Mature leaves are from 1⅛ to 1½ inches wide, and 2⅜ to 2½ inches long.

Veins: Prominent and lighter in color than leaf, running from the petiole to the tip, and having pinnate veins extending therefrom.

THE FLOWER

The plant first flowers in early December, with a heavy, almost simultaneous profusion of bloom by the third week of December. Thereafter, bloom is continuous through mid-March, with slight bloom thereafter. The flowers are borne 3 to 8 to a stem, regularly clustered, with flowers appearing at both the tips of the branches, and also to mid-branch, creating a very floriferous effect.

Form: Flowers are semi-double, hose-in-hose.

Petals: 5 upper petals and 5 lower petals, and at maturity are from 2½ to 3¼ inches wide, with a depth of 1½ to 1¾ inches.

Color: The flowers are predominantly in the White Group, Plate 155D, with a shading to the base of the corolla tube to Yellow Group, Plate 3D. In addition, rising from the base of the tube, there is a slight sprinkle of flecks of Red Group, Plates 51A to 51B.

Buds: Long, tapered, and in the White Group, Plate 155D, shading to the Yellow-Green Group, Plate 154D at the base.

Reproductive organs: 6 stamens in the White Group, Plate 155D, with pollen in the Yellow Group, Plate 2D and 3D. The stamens are from 1⅛ to 1¼ inches in length.

I claim:

1. A new and distinct variety of azalea plant which is a sport of Azalea "Rose Queen," and characterized in particular to novelty by the clean-looking white coloration of its flowers which grow profusely above and among rich green foliage; by the almost simultaneous full-bloom flowering toward the end of December; by its compact and thickly branched habit of growth; by its flowers which are larger than most other strains of azaleas; and by its greater resistance to rhizoctonia and other root diseases as established by comparison with other varieties grown in the same general area of the Irvine Ranch in southern California.

No references cited.

ROBERT E. BAGWILL, Primary Examiner